(12) United States Patent
Wu et al.

(10) Patent No.: US 8,304,565 B2
(45) Date of Patent: Nov. 6, 2012

(54) PEG-LIPID CONJUGATES FOR LIPOSOMES AND DRUG DELIVERY

(76) Inventors: Nian Wu, North Brunswick, NJ (US); Brian Charles Keller, Antioch, CA (US)

(*) Notice: Subject to any disclaimer, the term of this patent is extended or adjusted under 35 U.S.C. 154(b) by 375 days.

(21) Appl. No.: 12/456,046

(22) Filed: Jun. 10, 2009

(65) Prior Publication Data

US 2010/0076209 A1     Mar. 25, 2010

Related U.S. Application Data

(60) Provisional application No. 61/131,674, filed on Jun. 11, 2008, provisional application No. 61/135,515, filed on Jul. 21, 2008.

(51) Int. Cl.
*C07F 9/02*     (2006.01)

(52) U.S. Cl. ............. 554/79; 554/84; 554/101; 554/112
(58) Field of Classification Search ............. 554/79, 554/84, 101, 112
See application file for complete search history.

(56) References Cited

U.S. PATENT DOCUMENTS 7,803,397 B2 * 9/2010 Heyes et al. ............... 424/450

* cited by examiner

*Primary Examiner* — Deborah D Carr
(74) *Attorney, Agent, or Firm* — Buchanan Ingersoll & Rooney PC

(57) ABSTRACT

New diacylglycerol-polyethylene glycol (DAG-PEG) conjugates are described. A variety of linkers between the PEG chain and glycerol backbone of the DAG-PEGs may be selected to optimize liposomal formulations of pharmaceuticals and cosmetics.

5 Claims, 7 Drawing Sheets

PEG-LIPID CONJUGATES FOR LIPOSOMES AND DRUG DELIVERY

RELATED APPLICATIONS

This application claims priority to provisional U.S. patent application 61/131,674 entitled "PEG-LIPID CONJUGATES FOR LIPOSOMES AND DRUG DELIVERY" and filed on Jun. 11, 2008; and to provisional United States patent application 61/135,515 entitled "PEG-LIPID CONJUGATES FOR LIPOSOMES AND DRUG DELIVERY" and filed on Jul. 21, 2008.

FIELD OF THE INVENTION

This invention relates to lipids and liposomes. More particularly, the present invention relates to new PEG-lipid conjugates and their use to make liposomes for drug delivery, cosmetics and other purposes.

BACKGROUND OF INVENTION

Polyethylenglycol (PEG) is widely used as a water soluble carrier for polymer-drug conjugates. PEG is undoubtedly the most studied and applied synthetic polymer in the biomedical field [Duncan, R. *Nature Rev. Drug Discov.* 2003, 2, 347-360]. As an uncharged, water-soluble, nontoxic, nonimmunogenic polymer, PEG is an ideal material for biomedical applications. Covalent attachment of PEG to biologically active compounds is often useful as a technique for alteration and control of biodistribution and pharmacokinetics, minimizing toxicity of these compounds [Duncan, R. and Kopecek, J., *Adv. Polym. Sci.* 57 (1984), 53-101]. PEG possesses several beneficial properties: very low toxicity [Pang, S. N. J., *J. Am. Coil. Toxicol,* 12 (1993), 429-456], excellent solubility in aqueous solutions [Powell, G. M., *Handbook of Water Soluble Gums and Resins,* R. L. Davidson (Ed.), Ch. 18 (1980), MGraw-Hill, New York], and extremely low immunogenicity and antigenicity [Dreborg, S, *Crit. Rev. Ther. Drug Carrier Syst.,* 6 (1990), 315-365]. The polymer is known to be non-biodegradable, yet it is readily excretable after administration into living organisms. In vitro study showed that its presence in aqueous solutions has shown no deleterious effect on protein conformation or activities of enzymes. PEG also exhibits excellent pharmacokinetic and biodistribution behavior. [Yamaoka, T., Tabata, Y. and Ikada, Y., *J. Pharm. Sci.* 83 (1994), 601-606].

In the early developmental stage of PEGylation, the attention has been focused on the amino groups, which are the most represented groups in proteins and are the most suitable conjugation sites. Amino groups are generally exposed in an aqueous environment or other solvent, and can be modified with a wide selection of chemical strategies. Several conjugation strategies are now available, such as alkylation, which maintains the positive charge of the starting amino group because a secondary amine is formed, or acylation, accompanied by loss of charge. [Graham, L. M., *Adv. Drug Deliv. Rev.* 55 (2003), 1293-1302; Levy, Y. et al., *J. Pediatr.,* (1988) 113, 312-317; Bailon, P. et al., *Bioconjug. Chem.,* 12 (2001), 195-202; Wang, Y. S. et al., *Adv. Drug Deliv. Rev.* 54 (2002), 547-570; Kinstler, O. B. et al., *Pharm. Res.,* 13 (1996), 996-1002; Wong, S. S., *Chemistry of protein conjugation and cross-linking,* p. 13 (1991), CRC Press; Caliceti, P. et al., *J. Bioact. Comp. Polym.* 8 (1993), 41-50]

Esters with PEG have been utilized in chemical modifications of drugs. PEG esters which have an electron withdrawing substituent (alkoxy) in the a-position have proved to be especially effective linking groups in the design of prodrugs since the substituent aids in the rapid hydrolysis of the ester carbonyl bond, thus releasing alcohols in a continuous and effective manner. For instance, highly water soluble PEG-5000 esters of paclitaxel were synthesized and shown to function as prodrugs, i.e., breakdown occurred in a predictable fashion in vitro. [R. B. Greenwald, A. Pendri, D. Bolikal, C. W. Gilbert, *Bioorg. Med. Chem. Lett.,* 4 (1994), 2465-2470]. Studies also showed that amino acid conjugates appeared to be the most useful, reducing toxicity while increasing efficacy for most of the anticancer drugs [A. Pendri, C. D. Conover, R. B. Greenwald, *Anti-Cancer Drug Design,* 13 (1998), 387-395; R. B. Greenwald, A. Pendri, C. D. Conover, C. Lee, Y. H., Choe, C. Gilbert, A. Martinez, J. Xia, D. Wu, M. Hsue, *Bioorg. Med. Chem.,* 6 (1998), 551-562]

Thiol modification is another potentially useful strategy of PEGylation. For instance, nonessential amino acids in a protein sequence can be replaced by cysteine residues and can be replaced almost anywhere. Such mutant proteins have been generated to PEGylate therapeutically important drugs such as Granulocyte colony-stimulating factor (G-CSF) or human growth hormone (HGH) [Cox, G., Bolder Biotechnology, WO9903887; Berna, M. et al., 32nd *Annual meeting & exposition of the controlled release society,* 18-22 Jun. (2005), Abstract No. 415, Miami, USA]

Less specific linking strategies relied on the reduction of protein disulphide bridges with the aim of exposing new thiol groups have been used for the PEGylation of antibodies, as amino groups are not suitable as the modification sites because of the marked loss of recognition that occurs during the PEGylation procedure. However, disulphide bridges that link the IgG heavy chains can be cleaved, yielding an active Fab moiety with new exposed thiol groups where the sites of conjugation are also localized far from the antibodies recognition site. [A. P. Chapman et al., *Nat. Biotechnol.,* 17 (1999), pp. 780-783]

In recent years lipid conjugates to PEG have generated great interest, as a result of the discovery that incorporation of PEG-lipids into liposomes yields preparations with superior performance in comparison to conventional liposomes. Such liposomes remain in the blood circulation for extended periods of time and distribute through an organism relatively evenly with most of the dose remaining in the blood compartment and only 10-15% of the dose in liver. This constitutes a significant improvement over conventional liposomes. [Woodle, M. C. and Lasic, D. D., *Biochim. Biophys. Acta,* 1113 (1992), 171-199]. In these studies, amide-linked mPEG-DSPE (1,2-Distearoyl-sn-Glycero-3-Phosphoethanolamine) was prepared by coupling mPEG to the amino group of phosphatidyl ethanolamines [Parr, M. J., Ansell, S. M., Choi, L. S. and Cullis, P. R., *Biochim. Biophys. Acta,* 1195 (1994), 21-30] and the modified surface amino groups of DSPC-DPPE-cholesterol vesicles were reacted with mPEG-tresylate after liposome formation, instead of using a PEG-lipid conjugate to form liposomes [Senior, J., Delgado, C., Fisher, D., Tilcock, C. and Gregoriadis, *Biochim. Biophys. Acta,* 1062 (1991), 77-82]. The attractive feature of this approach is in its selective grafting of the polymer on the exterior of the vesicles, thus avoiding the presence of mPEG residues inside the liposomes. A similar study was reported, where grafting mPEG residues onto preformed liposomes, maleimido-PE-containing vesicles were prepared and then reacted with a thiol derivative of PEG [Herron, J. N., Gentry, C A., Davies, S. S., Wei. A. and Lin, J. N., *J. Controlled Rel.,* 28 (1994), 155-166].

Despite all this progress, significant potential for improved liposomal drug delivery remains. So far, few liposomal drugs have been approved for clinical use. Difficulties in obtaining suitable formulations of many drugs remain the challenges. Furthermore, it is desirable to develop new methods and materials to improve manufacturing, cell targeting, and drug release.

BRIEF SUMMARY OF THE INVENTION

New diacylglycerol-polyethylene glycol (DAG-PEG) conjugates are described. A variety of linkers between the PEG chain and glycerol backbone of the DAG-PEGs may be selected to optimize liposomal formulations of pharmaceuticals and cosmetics.

DETAILED DESCRIPTION OF PREFERRED EMBODIMENTS

Figure 1:
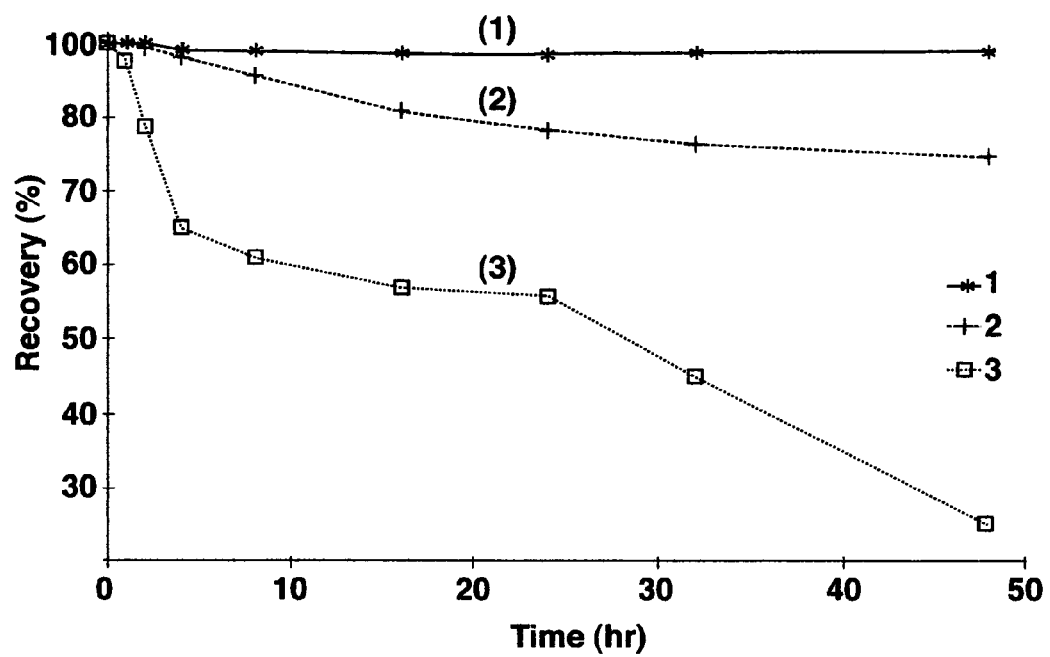
FIG. 1 shows stability profiles in a low pH medium of PEG (n=12)-3-acetyl-1,2-rac-dioleoylglycerol, PEG (n=12)-3-acetamido-dioleoylglycerol and PEG (n=12)-3-N-(mercaptomethyl)-Propionamido-1,2-rac dioleoylglycerol.

Embodiments of the present invention are described herein in the context of PEG-lipid conjugates for liposomes and drug delivery. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementation of the present invention.

In the interest of clarity, not all of the routine features of the implementations herein are described. It will be appreciated that in the development of such actual implementation, numerous implementation-specific details must be made in order to achieve the developer's specific goals, and that these specific goals will vary. Though such implementation might be complex, it will still be a routine exercise of engineering.

Herein, we describe biologically degradable linear PEG analogs carrying diacylglycerol lipid groups. These new molecules belong to a class referred to as diacylglycerol-polyethyleneglycols (DAG-PEGs). DAG-PEGs having certain properties form liposomes spontaneously upon mixing with an aqueous solution. Briefly, DAG-PEGs or lipid mixtures including DAG-PEGs must have packing parameters that allow liposome formation. Generally, $P_a$ is preferably between about 0.84 and 0.88, and $P_v$ is preferably between about 0.88 and 0.93. Also, the DAG-PEGs or lipid mixtures including DAG-PEGs must have a melting point below the temperature of liposome formation. If a DAG-PEG meets these conditions, it will form liposomes spontaneously (without external energy inputs). Spontaneous liposomes and DAG-PEGs are described in U.S. Pat. No. 6,6610,322, which is hereby incorporated by reference. The particular DAG-PEGs described in U.S. Pat. No. 6,6610,322 utilized a single oxy (alternatively called oxyl) linkage between the PEG and the glycerol backbone.

The present invention describes new linking chemical groups that can be selected to optimize and improve DAG-PEG liposome formulations. Selecting an appropriate linker between PEG and diacylglycerol can be important for several reasons, as described below.

Since a drug is a xenobiotic, the normal human body doesn't need it. Ideally, a drug should reach the site of action intact, cure the disease, and leave the body after it completes its mission. However, drug developers often face the dilemma that a potential drug is either metabolized or excreted from the body too fast, so that the drug can not reach its site of action and achieve its therapeutic effect, or too slow, so that it stays in the body for a long time causing side effects. An object of this invention is to develop PEG-lipids with unique linkers to help drugs to achieve therapeutic goals.

Liposomes can help drugs to penetrate cell membranes and to reach the site of action. They can also confer an advantage by reducing specific toxicities of some drugs, for example by reducing direct exposure of the drug to organs or tissues susceptible to damage. Further they can improve pharmacokinetics of a drug by delaying drug breakdown and clearance, serving as a sustained release drug depot, and also by targeting sites of disease. Liposomes may be delivered topically, orally, sublingually or by intravenous administration. Thus, liposome formulations must be optimized for each drug, disease, or route of administration. It is another object of this invention to provide new lipids to expand the range of possible liposome formulations.

Xenobiotics follow metabolic processes to be removed from the body. This process most commonly involves cytochrome P450 enzymes. These enzymes are a super family of proteins found in all living organisms. In humans, as well as all other mammalian species, this enzyme system is found principally in the liver but exists in all other organs and tissues. These enzymes catalyze the following reactions: aromatic hydroxylation; aliphatic hydroxylation; N-, O-, and S-dealkylation; N-hydroxylation; N-oxidation; sulfoxidation and deamination. Of particular importance to the present invention are the breakdown processes that the vesicles formed from news lipids, and the new lipids themselves, are expected to undergo. Methoxyl and methylamine groups are expected to undergo demethylation. Amines are expected to undergo N-oxidation or deamination. Sulfur bonds are expected to undergo S-oxidation. Esters and amides are expected to undergo hydrolysis. Since different organs and tissues have differing abilities to perform these different reactions, it is a further objective of the present invention to provide linkers with optimal degradation properties.

Similarly, different microenvironments within the body favor different breakdown processes. For example, acidic gastric fluids favors breakdown of thiol linkages. Therefore, it is still another object of this invention to provide new molecules for designing drug delivery formulations for diverse physiological microenvironments.

Of the two linked DAG-PEG components, diacylglycerol is digestible by humans while PEG is not. However, as mentioned earlier, PEG is readily excreted. Breaking the linkage between the two components may result in increased clearance for both. In is therefore an object of the invention to optimize clearance rates of lipid vesicles and lipids used for drug delivery.

Bilayer rigidity of liposomal drug formulations can be important to retain the drug within the liposome and to maintain liposomal integrity against clearance mechanisms of the body. Such rigidity can be manipulated by adding sterols, other excipients and/or by selecting acyl chains, though these methods result in a requirement for higher energy input during liposome formation. The present invention provides another means of controlling bilayer rigidity by selecting appropriate linkers. For example, due to the double bond character of the N, O or S with neighboring molecular bonds in some of these linkers, the barrier for rotation is very high resulting in more rigid liposomes. It is another object of the invention to provide new materials and methods to control rigidity of liposome membranes.

When using the lipids of the present invention to form spontaneous liposomes, the lipid mixtures used must fall within certain packing parameters. Since packing parameters of the DAG-PEGs depend on both the PEG portion and the diacylglycerol portion, breaking the link between the two results in a change of overall packing parameters. Such a phenomena can be used to control liposomal breakdown and drug release. It is therefore another object of the invention to control liposome breakdown and drug release by providing new DAG-PEGs with desirable degradation properties.

Furthermore, these new linking chemical groups in the PEG-lipids have larger polar surface areas than those having a single oxy linker. For some amphiphatic drugs or other compounds, this provides a better environment for the drug or other compounds to partition into the lipid bilayer of the vesicle.

Narrow molecular weight distribution of drug delivery polymers is crucially important for biomedical application, especially if used for intravenous injections. For instance, PEG-8 Caprylic/Capric Glycerides are mixtures of monoesters, diesters, and triesters of glycerol and monoesters and diesters of polyethylene glycols with a mean relative molecular weight between 200 and 400. Partially due to allergic reactions observed in animals, the application of PEG-8 CCG for many water-insoluble drugs was restricted and a dose limit of approximately 6% of PEG-8 CCG was posted for human oral drug formulations. (http://www.accessdata.fda.gov/scripts/cder/iig/getiigWEB.cfm)

In one aspect, the present invention employs a new platform known as click chemistry. [16. Binder, W. H.; Kluger, C. *Macromolecules*, 37 (2004), 9321-9330; Díaz, D. D.; Punna, S.; Holzer, P.; McPherson, A. K.; Sharpless, K. B.; Fokin, V. V.; Finn, M. G. *J. Polym. Sci., Part A: Polym. Chem.* 42, (2004), 4392-4403; Helms, B.; Mynar, J. L.; Hawker, C. J.; Frechet, J. M. J. *J. Am. Chem. Soc.*, 126 (2004), 15020-15021] Unlike free radical polymerization, the molecular weight distributions may be narrowly controlled, typically within 10% of the targeted PEG molecular weight. Monodistribution was achieved with purified PEGs. The well-defined PEG-diacylglycerol lipids prepared using this advanced technology may include all the various functional linker groups described herein.

A variety of new DAG-PEG lipids were synthesized and tested. The general structure of the new DAG-PEGs is

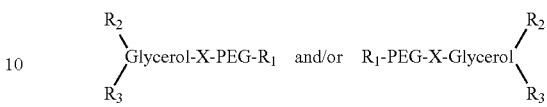

where $R_1$ is preferably either —OH or —OCH3; $R_2$ and $R_3$ are fatty acids including and not limited to laurate, oleate, myristate, palmitate, stearate and linoleate; and X represents a single linker or replicate linkers or combination of 2 or more listed linkers in between the lipid and PEG. Typically the $R_2$ and $R_3$ are the same, though they can also be different. If $R_2$ is located at C1 position, $R_3$ can be located at either C2 or C3 position of the glycerol. The general structure is meant to include all racemers and structural isomers of the structure, as they can be functionally equivalent.

Though $R_1$ is either —OH or —OCH$_3$ in the specific DAG-PEGs synthesized and described herein, in practice $R_1$ has a negligible effect on the overall DAG-PEG molecule and on liposome formation. Therefore, the invention includes DAG-PEGs where $R_1$ is selected from a wide variety of chemical moieties. Such moieties preferably have a molecular weight of less than 215, and more preferably a molecular weight of less than 45. Such moieties include —NH$_2$, —COOH, —OCH$_2$CH$_3$, —OCH$_2$CH$_2$OH, —COCH=CH$_2$, —OCH$_2$CH$_2$NH$_2$, —OSO$_2$CH$_3$, —OCH$_2$C$_6$H$_6$, —OCH$_2$COCH$_2$CH$_2$COONC$_4$H$_4$O$_2$, —CH$_2$CH$_2$=CH$_2$, and —OC$_6$H$_6$. Also $R_1$ may be a functional group that facilitates linking therapeutic or targeting agents to the surface of a liposome. Amino alkyl esters, maleimide, diglycidyl ether, maleinimido propionate, methylcarbamate, tosylhydrazone salts, azide, propargyl-amine, propargyl alcohol, NHS esters (e.g., propargyl NHS ester, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, R1 may include functional cell-targeting ligands such as folate, transferrin and molecules such as monoclonal antibodies, ligands for cellular receptors or specific peptide sequences can be attached to the liposomal surface to provide specific binding sites. R1 can include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethylaminium, butanoltrimethylaminium, dodecanoltrimethylaminium, hexanoltrimethylaminium, tetradecanoltrimethylaminium, hexadecanoltrimethylaminium, oleyltrimethylaminium, for example.

Table 1 describes the linkers ("X") used in the invention. Each of the linkers provides unique advantages for liposome formation and drug delivery. The structures shown in the table were mainly named by ChemDraw. In the event of minor variations of chemical names, the structures shown are meant to be controlling.

TABLE 1
| | | Linkers |
|---|---|---|
| No | Symbol X | |
| 1 | $N_1$ | 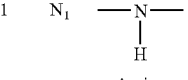 Amino |
| 2 | $N_2$ | 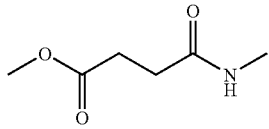 Succinylamino |
| 3 | $N_3$ | 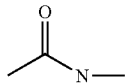 Acetamido |
| 4 | $N_4$ | 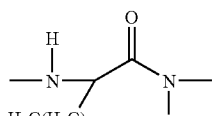 2-aminopentanamido |
| 5 | $N_5$ | 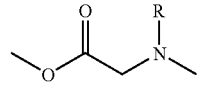 2 (2')-R'-aminoacetyl<br>R' = H or alkyl group etc. |
| 6 | $S_1$ | 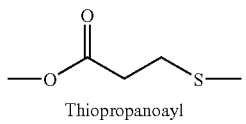 Thiopropanoayl |
| 7 | $S_2$ | 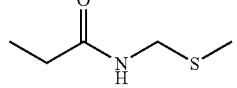 N-(mercaptomethyl)propionamido |
| 8 | $S_3$ | 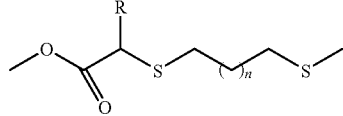 R = H or Alkyl group, n = 0 to 3<br>R = $CH_3$ and n = 1: 2-(3-mercaptopropylthio)propanoyl |
| 9 | $S_4$ | 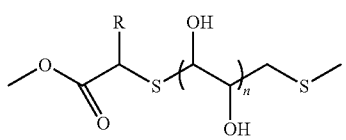 R = H or Alkyl group, n = 0 to 3<br>R = $CH_3$ and n = 1: 2-(1,2-dihydroxy-3-mercaptopropylthio)propanoyl |

TABLE 1-continued

| Linkers | | |
|---|---|---|
| No | Symbol X | |
| 10 | $Ac_1$ | 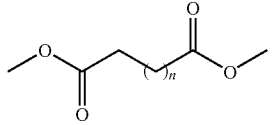<br>n = 1 to 3. n = 1: Succinyl |
| 11 | $Ac_2$ | 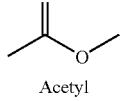<br>Acetyl |
| 12 | $Ac_3$ | 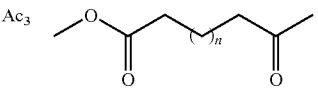<br>n = 0 to 3. n = 1: oxopentanoyl |
| 13 | $N_6$ | 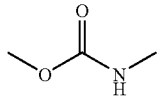<br>Carbamoyl |
| 14 | $N_7$ | 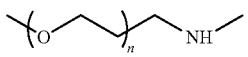<br>Aminoalkylol or Aminoalkyl, n = 0 to 2<br>n = 0: amino ($N_1$) |
| 15 | $N_8$ | 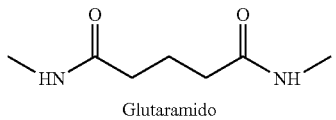<br>Glutaramido |
| 16 | $S_5$ | 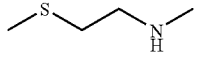<br>Aminoethanethiol |
| 17 | $S_6$ | 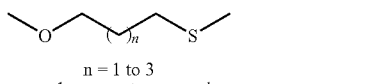<br>n = 1 to 3<br>n = 1: mercaptopropanol |
| 18 | $S_7$ | 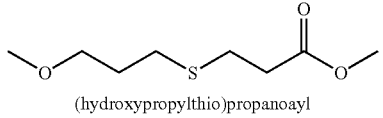<br>(hydroxypropylthio)propanoayl |
| 19 | $S_8$ | 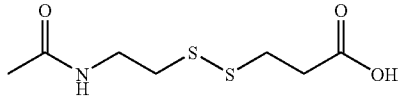<br>3-((2-propionamidoethyl)disulfanyl)propanoayl |
| 20 | $S_9$ | 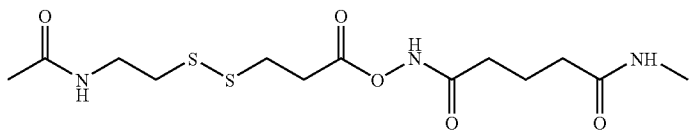<br>N'-(3-((2-acetamidoethyl)disulfanyl)propanoyloxy)glutaramido |

TABLE 1-continued

Linkers

| No | Symbol X | Structure |
|----|----------|-----------|
| 21 | $S_{10}$ | —N(R)—CH₂—C(=O)—S—; R = H or alkyl group etc. R = H: aminoethanethioate |
| 22 | $Ac_4$ | —O—CH₂—C(=O)—O—C(=O)—R—; R = —CH₂— or —O—; R = —CH₂: 2-hydroxyacetic propionic anhydride |

The invention can be practiced using a wide variety of fatty acids ($R_2$ and $R_3$). Table 2 lists some saturated lipids for use in the invention. Table 3 lists some unsaturated lipids for use in the invention.

TABLE 2

Saturated lipids for use in the invention:

| common name | IUPAC name | Chemical structure | Abbr. | Melting point (° C.) |
|---|---|---|---|---|
| Butyric | Butanoic acid | $CH_3(CH_2)_2COOH$ | C4:0 | −8 |
| Caproic | Hexanoic acid | $CH_3(CH_2)_4COOH$ | C6:0 | −3 |
| Caprylic | Octanoic acid | $CH_3(CH_2)_6COOH$ | C8:0 | 16-17 |
| Capric | Decanoic acid | $CH_3(CH_2)_8COOH$ | C10:0 | 31 |
| Lauric | Dodecanoic acid | $CH_3(CH_2)_{10}COOH$ | C12:0 | 44-46 |
| Myristic | Tetradecanoic acid | $CH_3(CH_2)_{12}COOH$ | C14:0 | 58.8 |
| Palmitic | Hexadecanoic acid | $CH_3(CH_2)_{14}COOH$ | C16:0 | 63-64 |
| Stearic | Octadecanoic acid | $CH_3(CH_2)_{16}COOH$ | C18:0 | 69.9 |
| Arachidic | Eicosanoic acid | $CH_3(CH_2)_{18}COOH$ | C20:0 | 75.5 |
| Behenic | Docosanoic acid | $CH_3(CH_2)_{20}COOH$ | C22:0 | 74-78 |

TABLE 3

Unsaturated lipids

| Name | Chemical structure | $\Delta^x$ Location of double bond | # carbon/double bonds |
|---|---|---|---|
| Myristoleic acid | $CH_3(CH_2)_3CH=CH(CH_2)_7COOH$ | cis-$\Delta^9$ | 14:1 |
| Palmitoleic acid | $CH_3(CH_2)_5CH=CH(CH_2)_7COOH$ | cis-$\Delta^9$ | 16:1 |
| Oleic acid | $CH_3(CH_2)_7CH=CH(CH_2)_7COOH$ | cis-$\Delta^9$ | 18:1 |
| Linoleic acid | $CH_3(CH_2)_4CH=CHCH_2CH=CH(CH_2)_7COOH$ | cis, cis-$\Delta^9$, $\Delta^{12}$ | 18:2 |
| α-Linolenic acid | $CH_3CH_2CH=CHCH_2CH=CHCH_2CH=CH(CH_2)_7COOH$ | cis, cis, cis-$\Delta^9$, $\Delta^{12}$, $\Delta^{15}$ | 18:3 |
| Arachidonic acid | $CH_3(CH_2)_4CH=CHCH_2CH=CHCH_2CH=CHCH_2CH=CH(CH_2)_3COOH^{NIST}$ | cis, cis, cis, cis- $\Delta^5\Delta^8$, $\Delta^{11}$, $\Delta^{14}$ | 20:4 |
| Erucic acid | $CH_3(CH_2)_7CH=CH(CH_2)_{11}COOH$ | cis-$\Delta^{13}$ | 22:1 |

A number of new DAG-PEGs were synthesized and tested. Most of the combinations of PEG chains and fatty acids were chosen because it was known or expected that such DAG-PEGs with oxy linkages would have packing parameters and melting points favorable for the formation of liposomes. The new DAG-PEGs are shown in Table 4.

TABLE 4

Characterization of Representative New DAG-PEG-Lipids

| Linker | Lipid | Melting point (° C.) | $P_a$ | $P_v$ | Spontaneous Liposome at 20° C. | Spontaneous Liposome at 37° C. |
|---|---|---|---|---|---|---|
| $N_1$ | PEG-12-$N_1$-GDO | Fluid @ 25 | 0.844 | 0.909 | Yes | Yes |
| $N_2$ | PEG-23-$N_2$-GDO | Fluid @ 25 | 0.859 | 0.890 | Yes | Yes |
| $N_3$ | PEG-18-$N_3$-GDO | Fluid @ 25 | 0.869 | 0.903 | Yes | Yes |
| $N_4$ | PEG-23-$N_4$-GDO | Fluid @ 25 | 0.847 | 0.892 | Yes | Yes |
| $S_1$ | PEG-8-$S_1$-GDO | Fluid @ 25 | 0.830 | 0.925 | Yes | Yes |

TABLE 4-continued

Characterization of Representative New DAG-PEG-Lipids

| Linker | Lipid | Melting point (° C.) | $P_a$ | $P_v$ | Spontaneous Liposome at 20° C. | Spontaneous Liposome at 37° C. |
|---|---|---|---|---|---|---|
| $S_2$ | PEG-18-$S_2$-GDO | Fluid @ 25 | 0.852 | 0.890 | Yes | Yes |
| $S_3$ | PEG-12-$S_3$-GDO | Fluid @ 25 | 0.847 | 0.892 | Yes | Yes |
| $Ac_1$ | PEG-18-$Ac_1$-GDO | Fluid @ 25 | 0.843 | 0.886 | Yes | Yes |
| $Ac_2$ | PEG-12-$Ac_2$-GDO | Fluid @ 25 | 0.848 | 0.883 | Yes | Yes |
| $N_1$ | PEG-12-$N_1$-GDM | Fluid @ 25 | 0.856 | 0.908 | Yes | Yes |
| $N_1$ | PEG-12-$N_1$-GDLO | Fluid @ 25 | 0.850 | 0.924 | Yes | Yes |
| $S_3$ | PEG-12-$S_3$-GDM | Fluid @ 25 | 0.854 | 0.886 | Yes | Yes |
| $S_3$ | PEG-12-$S_3$-GDLO | Fluid @ 25 | 0.855 | 0.899 | Yes | Yes |
| $Ac_2$ | PEG-12-$Ac_2$-GDM | Fluid @ 25 | 0.846 | 0.884 | Yes | Yes |
| $Ac_2$ | PEG-12-$Ac_2$-GDLO | Fluid @ 25 | 0.854 | 0.885 | Yes | Yes |
| $N_1$ | PEG-23-$N_1$-GDL | Fluid @ 25 | 0.866 | 0.919 | Yes | Yes |
| $N_1$ | PEG-12-$N_1$-GDP | Fluid @ 25 | 0.840 | 0.914 | Yes | Yes |
| $Ac_2$ | PEG-23-$Ac_2$-GDL | Fluid @ 25 | 0.842 | 0.872 | Yes | Yes |
| $Ac_2$ | PEG-12-$Ac_2$-GDP | Fluid @ 25 | 0.866 | 0.884 | Yes | Yes |

In Table 4 the symbols for the linkers are from Table 1. GDO means glycerol dioleate, GDM means glycerol dimyristate, GDLO means glycerol dilinoleate, GDL means glycerol dilaurate, and GDP means glycerol dipalmitate. The numeral after the PEG means the number of subunits in the PEG chain. For example, PEG-12 refers to a PEG chain having 12 subunits.

Packing parameters $P_a$ and $P_v$ were calculated using the following equation (Lasic D. D. "Liposomes: From Physics to Application," Elsevier, Amsterdam (1993), 49-51; Keller, C. B., Chapter 12, "Handbook of Cosmetic Science & Technology, edited Paye M., Barel, A. O., Maibach, H. I., Taylor & Francis, New York (2006), 165-174:

$$P_a = \eta \frac{F_a \lambda}{T_v} \text{ and } P_v = \eta \frac{F_v}{T_v}$$

where $\eta$ is a fraction factor which is related to the purity and homogeneity of the PEG-lipid ($\eta = \eta_1 + \eta_2 + \ldots = 1$). $F_a$ is the polar surface area of the lipid, $\lambda$ is length of lipophilic portion, $F_v$ and $T_v$ are the volumes of lipophilic portion and the whole molecule. ChemDraw (CambridgeSoft) and ChemSketch (Advanced Chemistry Development, Inc) were used to perform the calculations with the experimental data.

As described in U.S. Pat. No. 6,6610,322, combinations of lipids may be used to form liposomes if the packing parameters of the lipid combination as a whole are within favorable ranges. Thus, even PEG-lipid conjugates of the present invention which by themselves have packing parameters outside the desired range may be incorporated into liposomes by combining them with other lipids, or with other compounds such as sterols that affect overall packing parameters.

The use of new linkers between the C3 position of glycerol and the PEG chain did not significantly change the packing parameters or melting points of the new DAG-PEGS as compared to DAG-PEGs with oxy linkages. However due to the double bond character of the N, O or S with neighboring molecular bond in some of these linkers, the barrier for rotation is very high. The rate of conformational changes can be further lowered by involvement of these molecules in hydrogen bonding with neighboring molecules or fragments of the same molecules, giving rise to rigid conformers which may not be favorable for the formation of liposomes at an ambient temperature. In such case, longer formation time or elevated temperatures to increase the rate of liposome formations are necessary.

Liposomes incorporating PEG-lipid conjugates of the present invention may be used to encapsulate and deliver a wide variety of active agents since the liposomes include an enclosed aqueous space, a hydrophobic region in the bilayer, and sites for covalent attachment. Such active agents may include proteins, peptides, nucleic acids, antineoplastic agents, anti-inflammatories, anti-infectives, gastrointestinal agents, biological and immunological agents, dermatologic agents, ophthalmic and otic agents, diagnostic aids, nutrients and nutritional agents, hematological agents, endocrine and metabolic agents, cardiovasculars, renal and genitourinary agents, central nervous system agents.

The syntheses used in this invention to form diacylglycerol-polyethyleneglycols generally utilizes the reaction of the PEG polymer with a linker that is reactive with hydroxyl groups, typically anhydrides, acid chlorides, chloroformates and carbonates, aldehyde, esters, amides etc ore more efficient functional groups for the conjugation. Preferred end groups include maleimide, vinyl sulfones, pyridyl disulfide, amine, carboxylic acids and NHS esters.

The DAG-PEGs and linkers disclosed herein can be considered as a "tool kit" to aid in the design of lipsomes. The linkers described offer a variety of options in terms of size, potential binding sites, hydrogen bonding, polarity, and breakdown reactions. By selecting particular linkers, incorporation and retention of encapsulated agents can be improved. The lipophobic portion of amphiphatic molecules may be stabilized by selecting the appropriate linker. For example, linkers $Ac_4$ and $N_1$ differ greatly in their potentials to form hydrogen bonds.

The effective combination of functional head-groups, lipid chains and linker groups in membrane components can achieve controlled stability of the liposomal membrane and selective release of encapsulated material under specific environmental conditions. Degradation of the DAG-PEGs, with concurrent release of encapsulated compounds, can thus be controlled by selecting appropriate linkers. For instance, pH dependent hydrolysis of the non-charged cleavable linkers containing C—N or C—O bonds and the thiolysis of the linkers containing disulfide bonds that are integrated in the membrane occur. In some cases, release agents may expedite such breakdown. Examples of linkers whose breakdown rate is increased by release agents include: $S_8$, $S_9$, and $S_4$, which break down faster under hypoxic conditions; $S_2$, $S_{10}$, and $N_6$, which break down at high pH; and $S_8$ and $S_9$, which are sensitive to ultraviolet light. Catalysts may also increase the rate of breakdown of particular linkers. For example, $S_8$ and $S_9$ break down faster in the presence of $H^+$. Heat may increase the rate of acid-catalyzed linker degradation. FIG. 1 demonstrates enhanced breakdown of linker $S_2$ at low pH. It is worth noting that degradation may not be always a "breakdown," it is possible to form a secondary product under some conditions.

Even though degradation of some of the linkers occurs in the presence of release agents, the new DAG-PEGs of the invention are generally much more stable than phospholipids. For example, phospholipids degrade in a matter of days at room temperature while the new lipids are stable for long periods of time at room temperature.

Synthesis of the new lipids may be controlled so that there is a single linker in each DAG-PEG molecule. In some situations, however, it may be useful to have multiple copies of the same linker, or combinations of different linkers in a single molecule.

The liposomes of the present invention may be used for many applications. Formulation and delivery of pharmaceutical and cosmetic agents have been described. Additionally, the DAG-PEGs of the present invention may be used in other contexts where liposomes are advantages, for example industrial and/or cleaning processes.

In one aspect the invention includes a compound represented by the formula

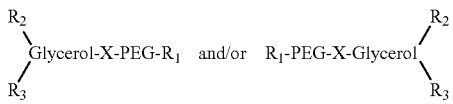

where $R_1$ preferably has a molecular weight of less than about 215; where $R_2$ and $R_3$ are alkyl groups having between 4 and 22 carbons; and where X is one or more linkers selected from the group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)disulfanyl)propanoyloxy)glutaramido, aminoethanethioate, and 2-hydroxyacetic proprionic anhydride. More preferably $R_1$ has a molecular weight of less than about 45. $R_1$ may be either —OH or —OCH$_3$. $R_2$ and $R_3$ may preferably be selected from the group consisting of oleate, myristate, linoleate and palmitate. The PEG chain may consist of between about 6 and 45 subunits. More preferably the PEG chain consists of between about 8 and 23 subunits. Still more preferably the PEG chain consists of between about 12 and 23 subunits. The compound is useful for applications other than liposomes, e.g., as a solvent.

In another aspect the invention includes a liposome comprising a compound represented by the formula

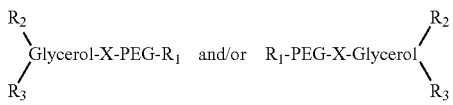

where $R_1$ preferably has a molecular weight of less than about 215; where $R_2$ and $R_3$ are alkyl groups having between 4 and 22 carbons; and
where X is selected from the group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)disulfanyl)propanoyloxy)glutaramido, aminoethanethioate, and 2-hydroxyacetic proprionic anhydride. More preferably $R_1$ has a molecular weight of less than about 45. $R_1$ may be either —OH or —OCH$_3$. $R_2$ and $R_3$ may be selected from the group consisting of oleate, myristate, linoleate and palmitate. It may be preferable to have molecular weight oligomers of PEG greater than 400 Da (or >8 subunits) since the lower molecular weight of PEG (i.e., <400 Da) have been shown to be degraded in vivo by alcohol dehydrogenase to toxic metabolites [Newman, J. Johnson et al., "Poly(ethylene glycol) Chemistry and Biological Applications," J. M. Harris and S. Zalipsky, Editors, ACS Books, Washington, D.C. (1997), 45-57]. However, some PEG-6 DAG-PEGs are useful for forming liposomes by themselves and in combination with other DAG-PEGs. Therefore, the PEG chain may consist of between about 6 and 45 subunits. More preferably the PEG chain may consist of between about 8 and 23 subunits. Even more preferably the PEG chain consists of between about 12 and 23 subunits. The liposome may comprise one or more active agents. The active agent may be a tetrahydrofuran. The active agent may be rifampicin.

In yet another aspect, the invention includes a method of preparing a liposome formulation of a therapeutic agent, the method comprising determining a therapeutic target; determining a mode of administration; determining the physiological conditions the liposome will encounter in reaching the therapeutic target using the mode of administration; selecting a DAG-PEG lipid having a linker between the PEG chain and the glycerol backbone, where such selecting is informed by the physiological conditions; and combining the DAG-PEG lipid and the therapeutic agent in a liposome formulation. The linker is selected from the group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)disulfanyl)propanoyloxy)glutaramido, aminoethanethioate, and 2-hydroxyacetic proprionic anhydride.

In another aspect the invention includes a DAG-PEG having the general structure

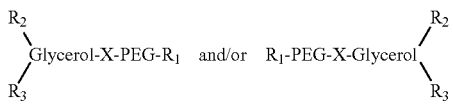

where $R_1$ has a molecular weight of less than about 215; where $R_2$ and $R_3$ are alkyl groups having between 4 and 22 carbons where X breaks done at an accelerated rate in the presence of a release agent selected from the group consisting of acid, hypoxia, light, and catalyst.

Another aspect of the invention includes a method of delivering a compound, where the method comprises preparing a liposome formulation of the compound, where the liposome comprises a DAG-PEG having a linker selected from the group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio) propanoayl, 3-((2-propionamidoethyl)disulfanyl)propanoayl, (((acetamidoethyl)disulfanyl)propanoyloxy)glutaramido, aminoethanethioate, and 2-hydroxyacetic proprionic anhydride; locating the liposome at a desired site; and providing a release agent, where the release agent causes the linker to degrade. The release agent may be an acid, light, hypoxia, or a catalyst.

EXAMPLES

Chemicals and Reagents: N,N'-dicyclohexylurea, N,N'-dicyclohexylcarbodiimide, DL 1,2-rac-dioleoylglycerol, sodium cyanoborohydride, dimethyl sulfoxide (DMSO) and other chemicals were obtained from Sigma-Aldrich (St. Louis, Mo., USA). Activated PEG polymers including poly(ethylene glycol)$_{12}$-aldehyde, poly(ethylene glycol)$_{12}$-succinyl-D,L-dithiothreitol, Poly(ethylene glycol)$_{12}$-monomethyl ether succinate and 3-amino-1,2-rac-dioleoyl glycerol were supplied by Novus PharmTech, Ltd (Nanjing, China). Bulk quantity of DL 1,2-rac-dioleoylglycerol is commercially available and can be purchased from Spectrum Chemicals (Gardena, Calif., USA).

Example 1

Synthesis of PEG-amino ($N_1$)-GDO 3-amino-1,2-rac-dioleoyl glycerol (~8 moles) and potassium hydroxide (KOH, 0.5 moles) were charged into a reactor. The reaction mixture was heated to a temperature of 120-130° C. under nitrogen for two hours, with ethylene oxide (in an amount calculated to result in polymers with an average chain length of eight subunits) added while held at a temperature of 120-130° C. The reaction was completed when free ethylene oxide was not detectable. The resulting brine was continuously extracted, typically for 4 hours at 55° C. with ethyl acetate. The product was dried out of the solvents under vacuo.

Example 2

Synthesis of PEG-12-Succinylamino ($N_2$)-GDO

A mixture of 3-amino-1,2-rac-dioleoyl glycerol (0.1 mol); poly(ethylene glycol)$_{12}$-monomethyl ether succinate (0.1 mol); N,N'-dicyclohexylcarbodiimide (0.1 mol); and a catalytic amount of 4-dimethylaminopyridine in anhydrous Dichloromethane (200 ml) was stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents and discarded. The peg-lipid peak at 220 nm (UV monitoring) was collected. Free PEGs were washing out the column by 100% acetone. The product was dried out of the solvents under vacuo.

Example 3

Synthesis of PEG-12-Acetamido ($N_3$)-GDO 3-amino-1,2-rac-dioleoyl glycerol was dissolved in ethanol/50 mM sodium phosphate (1/1, v/v). The final concentration was 0.1 molar. Poly(ethylene glycol)$_{12}$-aldehyde (0.5 mol) were added to the solution, the pH was adjusted to 8.0, stirred at room temperature for 20 h. The product was purified on a C8 column, using acetonitrile/10 mM ammonium acetate, pH 6.6, then a linear gradient of methanol from 60 to 100% in 15 min, followed by a 10 min isocratic step with 100% methanol as the elution system. Peaks were detected for collection at 220 nm. The collected fraction was then freeze-dried.

Example 4

Synthesis of PEG-12-Aminopentanamido ($N_4$)-GDO 3-amino-1,2-rac-dioleoyl glycerol was dissolved in ethanol/0.2M borate buffer, pH 8.5, 1/1 (final concentration 0.5 g/mL), and a 5-fold excess of poly(ethylene glycol)$_{12}$ norleucine-N-hydroxysuccinimide (Sartore, L., Caliceti, P., Schiavon, O., Monfardini, C., and Veronese, F. M., Accurate evaluation method of the polymer content in monomethoxypoly (ethylene glycol) modified proteins based on amino acid analysis. *Appl. Biochem. Biotechnot* 31(1991), 213-222) was added while stirring. The reaction was over after 6 h at room temperature, as confirmed by analytical RP-HPLC. The product was purified on a C8 column, using acetonitrile/50 mM ammonium acetate, pH 6.5, then a linear gradient of methanol from 60 to 100% in 15 min, followed by a 10 min isocratic step with 100% methanol as the elution system. Peaks were detected for collection at 220 nm. The collected fraction was then freeze-dried.

Example 5

Synthesis of PEG-12-Aminoacetyl ($N_5$)-GDO 3-amino-1,2-rac-dioleoyl glycerol was dissolved in ethanol/50 mM sodium phosphate (1/1, v/v). The final concentration was 0.1 molar. Poly(ethylene glycol)$_{12}$-aldehyde (0.5 mol) and sodium cyanoborohydride (0.2 mol) were added to the solution, the pH was adjusted to 8.0, and the mixture was stirred at room temperature for 20 h. The product was purified on a C8 column, using acetonitrile/10 mM ammonium acetate, pH 6.6, as elution systems. Peaks were detected at 220 nm. A linear gradient of methanol from 60 to 100% in 15 min was used, followed by a 10 min isocratic step with 100% methanol. The collected fraction was then freeze-dried.

Example 6

Synthesis of PEG-12-Thiopropanoyl ($S_1$)-GDO mPEG 600 (0.5 moles) in 150 mL of DMF, was reacted with 3-mercaptopropionic acid (10 mol, 20 equiv) in the presence 2,T-azobisisobutyronitrile (1 mol equiv). The reaction mixture was stirred at 65° C. for 24 h under argon atmosphere. The polymer was precipitated twice in a large excess of ether. The resulting white product was dissolved into methanol, and potassium hydroxide (1 mol equiv) dissolved in water was added. The mixture was stirred for approximately 4 h. Then, methanol was partially evaporated and diluted with water (100 mL) and extracted by dichloromethane (5×100 mL). The combined organic layer was dried over $Na_2SO_4$, filtered, and concentrated to 1/100 of the initial volume. The polymer was reprecipitated from an excess volume of ether and freeze-dried from benzene to and transferred to the next step. The transferred resultant (0.1 mol), dioleoyl glycerol (0.1 mol), N,N'-dicyclohexylcarbodiimide (0.1 mol) and a catalytic amount of 4-dimethylaminopyridine in anhydrous Dichloromethane (200 ml) was stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents and discarded. The peg-lipid peak at 220 nm (UV monitoring) was collected. Free PEGs were washing out the column by 100% acetone. The product was dried out of the solvents under vacuo.

Example 7

Synthesis of PEG-12-(mercaptomethyl)propionamido ($S_2$)-GDO mPEG 600 (0.91 mmol) was freeze dried from benzene and mixed with the solution a solution of DMF (50 mL) containing 2-aminoethanethiol hydrochloride (1.87 mol, 20 equiv) and 2,2'-azobisisobutyronitrile (1 mol equiv). The reaction mixture was stirred at 65° C. for 24 h under argon atmosphere. The polymer was precipitated twice in a large excess of ether. The resulting white product was dissolved into methanol, and 5.1 mg (1 equiv) of potassium hydroxide dissolved in water was added. The mixture was stirred for approximately 4 h. Then methanol was partially evaporated and the mixture was diluted with water (30 mL) and extracted by dichloromethane (5×80 mL). The combined organic layer was dried over $Na_2SO_4$, filtered, and concentrated to 1/100 of the initial volume. The polymer was reprecipitated from an excess volume of ether and then freeze-dried from benzene and transferred to the next step. The transferred resultant (0.1 mol), dioleoyl glycerol (0.1 mol), N,N'-dicyclohexylcarbodiimide (0.1 mol) and a catalytic amount of 4-dimethylaminopyridine in anhydrous Dichloromethane (200 ml) was stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents and discarded. The peg-lipid peak at 220 nm (UV monitoring) was collected. Free PEGs were washed out the column by 100% acetone. The product was dried out of the solvents under vacuo.

Example 8

Synthesis of PEG-12-2-(3-mercaptopropylthio)propanoyl ($S_3$)-GDO mPEG-1,2-ethanedithiol-propanoate was prepared by a Michael type polyaddition of mPEG 600 methyl acrylate with 1,2-ethanedithiol. 1,2-ethanedithiol-(3.1313 mol) was dissolved in 300 mL of DMSO at room temperature. mPEG 600 methyl acrylate (3.1310 mol) was added to the DMSO solution. Triethanolamine (0.04 mol) was added dropwise to the solution. The solution was stirred at room temperature for 72 h. The polymer was precipitated in ether and further purified by repeated precipitation. The precipitate was dried in a vacuum oven at 70° C. overnight and transferred to the next step. mPEG-1,2-ethanedithiol-propanoate (0.5 mol) and succinic dioleoylglycerol (0.5 mol) were dissolved in 100 mL of dry DMSO and stirred at 60° C. for 72 h until all hydroxyl groups were reacted. The resulting PEG-$S_3$-lipid was isolated in ether and dried under a high vacuum at 60° C. overnight. Crude product in brine was continuously extracted, typically for 4 hours at 55° C. with ethyl acetate. The product was dried out of the solvents under vacuo.

Example 9

Synthesis of PEG-12-2-(1,2-dihydroxy-3-mercapto-propylthio)propanoyl ($S_4$)-GDO mPEG-D,L-dithiothreitol-propanoate was prepared by a Michael type polyaddition of mPEG 600 methyl acrylate with D,L-dithiothreitol. 1,2-ethanedithiol-(3.1313 mol) was dissolved in 300 mL of DMSO at room temperature. mPEG 600 methyl acrylate (3.1310 mol) was added to the DMSO solution. Triethanolamine (0.04 mol) was added dropwise to the solution. The solution was stirred at room temperature for 72 h. The polymer was precipitated in ether and further purified by repeated precipitation. The precipitate was dried in a vacuum oven at 70° C. overnight and transferred to the next step. mPEG-1,2-D,L-dithiothreitol-propanoate (0.5 mol) and succinic dioleoylglycerol (0.5 mol) were dissolved in 100 mL of dry DMSO and stirred at 60° C. for 72 h until all hydroxyl groups were reacted. The resulting PEG-$S_3$-lipid was isolated in ether and dried under a high vacuum at 60° C. overnight. Crude product in brine was continuously extracted, typically for 4 hours at 55° C. with ethyl acetate. The product was dried out of the solvents under vacuo.

Example 10

Synthesis of PEG-12-Succinyl ($Ac_1$)-GDO

Dioleoyl glycerol (0.1 mol), poly(ethylene glycol)$_{12}$-monomethyl ether succinate (0.1 mol), N,N'-dicyclohexylcarbodiimide (0.1 mol) and a catalytic amount of 4-dimethylaminopyridine in anhydrous Dichloromethane (200 ml) was stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first eluted fraction was unreacted reagents, and was discarded. The PEG-lipid peak at 220 nm (UV monitoring) was collected. Free PEGS were washed out the column by 100% acetone. The product was dried out of the solvents under vacuo.

Example 11

Synthesis of PEG-12-Acetyl ($Ac_2$)-GDO

Dioleoyl glycerol (0.1 mol), monocarboxylpoly(ethylene glycol)$_{12}$-monomethyl ether (0.1 mol), N,N'-dicyclohexylcarbodiimide (0.1 mol) and a catalytic amount of 4-dimethylaminopyridine in anhydrous Dichloromethane (200 ml) was stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first eluted fraction was unreacted reagents, and was discarded. The peg-lipid peak at 220 nm. (UV monitoring) was collected. Free PEGs were washed out the column by 100% acetone. The product was dried out of the solvents under vacuo.

Example 12

Synthesis of PEG-12-5-oxopentanoyl ($Ac_3$)-GDO

Dioleoyl glycerol (0.1 mol), mono-5-oxopentanoyl poly(ethylene glycol)$_{12}$-monomethyl ether (0.1 mol), N,N'-dicyclohexylcarbodiimide (0.1 mol) and a catalytic amount of 4-dimethylaminopyridine in anhydrous Dichloromethane (200 ml) were stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents, and was discarded. The peg-lipid peak at 220 nm (UV monitoring) was collected. Free PEGs were washed out the column by 100% acetone. The product was dried out of the solvents under vacuo.

Example 13

Synthesis of PEG-12-hydroxyacetic propionic anhydrido ($Ac_4$)-GDO

Dioleoyl glycerol (0.1 mol), 2-hydroxyacetic 2-(mPEG-12)-acetic anhydride (0.1 mol), N,N'-dicyclohexylcarbodiimide (0.1 mol) and a catalytic amount of 4-dimethylaminopyridine in anhydrous Dichloromethane (200 ml) were stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents, and was discarded. The peg-lipid peak at 220 nm (UV monitoring) was collected. Free PEGs were washed out the column by 100% acetone. The product was dried out of the solvents under vacuo.

Example 14

Synthesis of PEG-12-Carbamoyl ($N_6$)-GDO 3-hydroxyl-1,2-rac-dioleoyl glycerol was dissolved in DMF. The final concentration was 0.1 molar. Poly(ethylene glycol)$_{12}$-aminoacetic acid (0.1 mol), and a catalytic amount of 4-dimethylaminopyridine in anhydrous DMF were added to the solution and stirred at room temperature for 24 h. The product was purified on a C8 column, using acetonitrile/10 mM ammonium acetate, pH 6.6, a linear gradient of methanol from 60 to 100% in 15 min, followed by a 10 min isocratic step with 100% methanol as the elution system. Peaks were detected at 220 nm. And collected. The collected fraction was then freeze-dried.

Example 15

Synthesis of PEG-12-$N_7$-GDO

The synthesis was same as for PEG-12-Amino ($N_1$)-GDO.

Example 16

Synthesis of PEG-12-glutaramido ($N_8$)-GDO

Methoxy-PEG 600 N-succinimidyl ester (0.1 mol) and 3 mL of triethylamine were added to a solution of 3-amino-1,2-rac-dioleoyl glycerol (0.1 mol) in 250 mL of $CHCl_3$, and the reaction mixture was stirred for 2 hours at 15° C. The solvent was evaporated, and the residue was dissolved in 100 mL of $CHCl_3$ and purified by chromatography on 200 g of silica gel. Elution was with with 250 mL of $CHCl_3$/MeOH, 90/10 (v/v) and 250 mL of $CHCl_3$/MeOH, 70/30 (v/v).

Example 17

Synthesis of PEG-12-mercaptopropanol ($S_5$)-GDO

Allyl-PEG 600 (0.1 mol) was mixed with the solution in DMF (500 mL) containing 3-ethanethiol-dl-1,2-dioleoyl glycerol (0.1 mol, 1 equiv) and 2,2'-azobisisobutyronitrile (0.1 mol, 1 equiv). The reaction mixture was stirred at 65° C. for 24 h under argon atmosphere. The polymer was precipitated twice in a large excess of ether. The resulting white product was dissolved into methanol, and 5.1 mg (1 equiv) of potassium hydroxide dissolved in water was added. The mixture was stirred for approximately 4 h, then diluted with water (100 mL) and extracted by dichloromethane (5×150 mL). The combined organic layer was dried over $Na_2SO_4$, filtered, and concentrated to 1/100 of the initial volume. The polymer was reprecipitated from an excess volume of ether and freeze-dried from benzene.

Example 18

Synthesis of PEG-12-(hydroxypropylthio)propanoayl ($S_6$)-GDO

Allyl-PEG 600 (0.1 mol) was mixed with the solution in DMF (500 mL) containing 3-mercaptopropionic acid-dl-1,2-dioleoyl glycerol (0.1 mol, 1 equiv) and 2,2'-azobisisobutyronitrile (0.1 mol, 1 equiv). The reaction mixture was stirred at 65° C. for 24 h under argon atmosphere. The polymer was precipitated twice in a large excess of ether. The resulting white product was dissolved into methanol, and 5.1 mg (1 equiv) of potassium hydroxide dissolved in water was added. The mixture was stirred for approximately 4 h, then diluted with water (100 mL), and extracted by dichloromethane (5×150 mL). The combined organic layer was dried over $Na_2SO_4$, filtered, and concentrated to 1/100 of the initial volume. The polymer was reprecipitated from an excess volume of ether and freeze-dried from benzene to yield a yellowish liquid.

Example 19

Synthesis of PEG-12-mercaptopropanoayl ($S_7$)-GDO

Poly(ethylene glycol) 750 methacrylate (0.1 mol) was mixed with the solution in DMF (500 mL) containing 3-ethanethiol-dl-1,2-dioleoyl glycerol (0.1 mol, 1 equiv) and 2,2'-azobisisobutyronitrile (0.1 mol, 1 equiv). The reaction mixture was stirred at 65° C. for 24 h under argon atmosphere. The polymer was precipitated twice in a large excess of ether. The resulting white product was dissolved into methanol, and 5.1 mg (1 equiv) of potassium hydroxide dissolved in water was added. The mixture was stirred for approximately 4 h, then diluted with water (100 mL), and extracted by dichloromethane (5×150 mL). The combined organic layer was dried over $Na_2SO_4$, filtered, and concentrated to 1/100 of the initial volume. The polymer was reprecipitated from an excess volume of ether and freeze-dried from benzene to yield a yellowish liquid.

Example 20

Synthesis of PEG 12-3-((2-propionamidoethyl)disulfanyl)propanoayl ($S_8$)-GDO

A solution of PEG-12-3-((2-propionamidoethyl)disulfanyl)propanoic acid (0.2 mol) in 250 mL of dry pyridine (pre-dried by placing 4 Angstrom molecular sieves into reagent grade pyridine, shaking and letting stand at least overnight) was stirred at room temperature under an argon atmosphere. A solution of 3-amino-1,2-rac-dioleoyl glycerol (0.2 mmol) in 50 mL of dry Pyridine was added dropwise over a period of 30 min. The solution was stirred for an additional 60 min, 10 mL of acetic acid was added, and the solvent was evaporated. Residual acetic acid was azeotroped with toluene. The residue was dissolved in 100 mL of $CHCl_3$ and subjected to chromatography on 500 g of silica gel. The product was eluted by first applying 500 mL of $CHCl_3$/MeOH/AcOH=90/10/0.1 and then 600 mL of 70/30/0.5. Fractions containing the product were pooled, evaporated, and azeotroped with toluene. The residue was again dissolved in $CHCl_3$, filtered, and evaporated to yield a yellowish liquid.

Example 21

Synthesis of PEG 12-$N^1$-(3-((2-acetamidoethyl)disulfanyl)propanoyloxy)-glutar amido ($S_9$)-GDO A solution of PEG-12-2,5-dioxopyrrolidin-1-yl 3-((2-acetamidoethyl)disulfanyl)-propanoate (0.2 mol) in 250 mL of dry Pyridine (pre-dried by placing 4 Angstrom molecular sieves into reagent grade Pyridine, shaking and letting stand at least overnight) was stirred at room temperature under an argon atmosphere. A solution of 3-amino-1,2-rac-dioleoyl glycerol (0.2 mmol) in 50 mL of dry pyridine was added dropwise over a period of 30 min. The solution was stirred for an additional 60 min, 10 mL of acetic acid was added, and the solvent was evaporated. Residual acetic acid was azeotroped with toluene. The residue was dissolved in 100 mL of $CHCl_3$ and subjected to chromatography on 500 g of silica gel. The product was eluted by first applying 500 mL of $CHCl_3$/MeOH/AcOH=90/10/0.1 and then 600 mL of 70/30/0.5. Fractions containing the product were pooled, evaporated, and azeotroped with toluene. The residue was again dissolved in $CHCl_3$, filtered, and evaporated to yield a yellowish liquid.

Example 22

Synthesis of PEG 12-aminoethanethioayl ($S_{10}$)-GDO

Allyl-PEG 600 (0.1 mol) was mixed with the solution in DMF (500 mL) containing dl-1,2-dioleoyl glycerol-3-amino-ethanethioic S-acid (0.1 mol, 1 equiv) and 2,2'-azobisisobutyronitrile (0.1 mol, 1 equiv). The reaction mixture was stirred at 65° C. for 24 h under argon atmosphere. The polymer was precipitated twice in a large excess of ether. The resulting white product was dissolved into methanol, and 5.1 mg (1 equiv) of potassium hydroxide dissolved in water was added. The mixture was stirred for approximately 4 h, then diluted with water (100 mL), and extracted by dichloromethane (5×150 mL). The combined organic layer was dried over $Na_2SO_4$, filtered, and concentrated to 1/100 of the initial volume. The polymer was reprecipitated from an excess volume of ether and freeze-dried from benzene.

Example 23

Synthesis of PEG-12-hydroxyacetic propionic anhydrido ($Ac_4$)-GDO

Dioleoyl glycerol (0.1 mol), 2-hydroxyacetic 2-(mPEG-12)-acetic anhydride (0.1 mol), N,N'-dicyclohexylcarbodiimide (0.1 mol) and a catalytic amount of 4-dimethylaminopyridine in anhydrous Dichloromethane (200 ml) were stirred at room temperature for 24 h, after which the N,N'-dicyclohexylurea salts were precipitated and removed by filtration. The filtrates were evaporated under reduced pressure. The crude product was purified by chromatography on a silica gel (G60, grade 60, mesh 240-400) column. The column was eluted with a 1:1 (v/v) diethyl ether/acetone mixture. The first fraction eluted was unreacted reagents, and was discarded. The peg-lipid peak at 220 nm (UV monitoring) were collected. Free PEGs were washing out the column by 100% acetone. The product was dried out of the solvents under vacuo.

Example 24

In Vitro Stability of Selective Linkers

Three DAG-PEGs with equivalent PEG chains and fatty acids, but different linkages (shown in Table 5) were tested for stability at low pH, in the range of 1.4 to 2.1. Table 5 includes alternate names for each of the three DAG-PEGs tested.

TABLE 5

| DAG-PEGs with different linkages | |
|---|---|
| Linker | Names |
| $Ac_2$ | PEG (n = 12)-3-acetyl-1,2-rac-dioleoylglucerol<br>PEG-12-$Ac_2$-GDO (glycerol dioleate) |
| $N_3$ | PEG (n = 12)-3-acetamido-dioleoylglycerol<br>PEG-12-$N_3$-GDO (glycerol dioleate) |
| $S_2$ | PEG (n = 12)-3-N-(mercaptomethyl)-Propionamido-1,2-rac dioleoylglucerol<br>PEG-12-$S_2$-GDO (glycerol dioleate) |

The selected DAG-PEGs were mixed with 10 mM phosphate buffer (pH 2.1) at final concentrations approximately 0.05 g/mL and incubated at 37°. The sample solutions were tested on a GPC column with RI detector and the breakdown fragments were further confirmed by LC-MS/MS. The stability profiles are presented in FIG. 1.

In FIG. 1, (1) is PEG (n=12)-3-acetyl-1,2-rac-dioleoylglucerol, (2) is PEG (n=12)-3-acetamido-dioleoylglycerol and (3) is PEG (n=12)-3-N-(mercaptomethyl)-Propionamido-1,2-rac-dioleoylglucerol. (1) was stable, (2) was relatively stable, and (3) degraded quickly at a low pH (in the range of human gastric pH, i.e., 1.4 to 2.1).

Example 25

Biocompatibility Experiments on DAG-PEGs

The use of adequate target cells for cytotoxicity testing of biomedical materials has often been experimentally assessed with respect to the clinical relevance of the test results. An evaluation of new synthetic PEG-lipids with regard to biocompatibility is critically important for judging the potential of new materials in biological-related applications. Thus, the cytotoxicity of the novel PEG-lipids was evaluated qualitatively by minimal essential medium testing with L929 cell line. This was accomplished by first introducing the lipids with fresh 10% bovine serum (pH 7.2) to give a final concentration of 5 mg/mL. The samples were then sterilized and extensively washed three times with sterile sodium chloride-phosphate buffer (pH 7.4) prior to transfer to individual 24-well tissue culture plates. Aliquots (1 mL) of mouse fibroblasts (L929) suspension with $1.5 \times 10^4$ cell/mL were seeded on the sample membranes. After 48 h of culture, cellular constructs were harvested, rinsed twice with sodium chloride-phosphate buffer to remove free cells, and adherent cells were fixed with 3.0% glutaraldehyde at 4° C. for 5 h. The samples were dehydrated through repeated rinsing with alcohol solutions and air-dried overnight. Dry samples were coated with gold for observation of cell morphology on the surface of the scaffolds by SEM. No qualitative change in monolayer confluence and morphology was observed in the polyester samples relative to the positive control, indicating negligible cytotoxic response of the cells to the PEG-grafted lipids. Similar results were obtained for all PEG-lipids tested.

In addition, hemolysis of human red blood cells was performed to provide a more quantitative cytotoxicity evaluation of the PEG-grafted lipids. Cell lysis caused by cytotoxic material leads to release of heme into solution, which was detected by absorbance at 413 nm and compared to control experiments performed in the absence of the synthetic material. Results in Table 6 for equivalent concentrations (20 mmol) of sodium lauryl sulfate (SLS) and mPEG-600 were shown for the comparison. Less than 1.6% lysis was observed for all PEG-grafted lipids, with the lowest value (0.3%) measured for PEG $12-N_3$-GDO. These results were significantly lower than PEG 600 monomethyl ether, the starting material (3.5%) and dramatically lower than those obtained for the surfactant SLS (80%), used as a comparative control.

TABLE 6

| Comparison of Hemolysis | | |
|---|---|---|
| Linker | Lipid | % Hemolysis |
| Control 1 | mPEG 600 | 3.5 |
| Control 2 | SLS | 80 |
| $N_1$ | PEG-12-$N_1$-GDO | 0.3 |
| $N_2$ | PEG-23-$N_2$-GDO | 0.5 |
| $N_3$ | PEG-18-$N_3$-GDO | 0.3 |
| $N_4$ | PEG-23-$N_4$-GDO | 0.7 |
| $S_1$ | PEG-8-$S_1$-GDO | 1.5 |
| $S_2$ | PEG-18-$S_2$-GDO | 1.2 |
| $S_3$ | PEG-12-$S_3$-GDO | 1.5 |
| O | PEG-12-oxy-GDO | 1.6 |
| $Ac_1$ | PEG-18-$Ac_1$-GDO | 1.0 |
| $Ac_2$ | PEG-12-$Ac_2$-GDO | 1.1 |
| $N_1$ | PEG-12-$N_1$-GDM | 0.4 |
| $N_1$ | PEG-12-$N_1$-GDLO | 0.3 |
| $S_3$ | PEG-12-$S_3$-GDM | 1.5 |
| $S_3$ | PEG-12-$S_3$-GDLO | 1.5 |
| $Ac_2$ | PEG-12-$Ac_2$-GDM | 1.0 |
| $Ac_2$ | PEG-12-$Ac_2$-GDLO | 0.9 |
| $N_1$ | PEG-23-$N_1$-GDL | 0.3 |
| $N_1$ | PEG-12-$N_1$-GDP | 0.3 |
| $Ac_2$ | PEG-23-$Ac_2$-GDL | 0.8 |
| $Ac_2$ | PEG-12-$Ac_2$-GDP | 0.9 |

Example 26

Rifampicine IV Injectable Solution

DAG-PEG lipid was added to a vessel equipped with a mixer propeller. The drug substance was added with constant mixing. Mixing continued until the drug was visually dispersed in the lipids. Pre-dissolved excipients were slowly added to the vessel with adequate mixing. Mixing continued until fully a homogenous solution was achieved. A sample formulation is described in Table 7, the targeted pH range was between 6.5 and 8.

TABLE 7

| Ingredient | mg/mL |
|---|---|
| Rifampicine | 4.0 |
| PEG Lipid | 40 |
| Sodium Hydroxide | See Below |
| Lactic Acid | 50 |
| Purified Water | qs 1 mL |

The lipid may be PEG 12-GDO (oxyl linkage), PEG-12-acetamido ($N_2$)-GDO, PEG 12-GDM (oxyl linkage), PEG-12-acetamido ($N_2$)-GDM, PEG 12-$N_3$-GDLO, PEG 12-GDLO (oxyl linkage) or any combination thereof Sodium hydroxide (NaOH) is used to prepare a 10% w/w solution in purified water, and NaOH is used to adjust pH if necessary. The targeted pH is in a range of 6.5.0 to 8.0.

Example 27

Bioavailability of Rifampicine Formulations

Groups of three male mice (B6D2F1) were used for the studies. Pharmacokinetics (PK) were performed on heparinized mouse plasma samples obtained typically at 0 hr, 0.08 hr, 0.25 hr, 0.5 hr, 1 hr, 2 hr, 4 hr, 8 hr, 16 hr and 24 hr after the bolus IV injection. Samples were analyzed using a HPLC-MS method. To determine the level of each drug, the drug was first isolated from plasma with a sample pre-treatment. Acetonitrile were used to remove proteins in samples. An isocratic HPLC-MS method was then used to separate the drugs from any potential interference. Drug levels were measured by MS detection with a multiple reaction monitoring (MRM) mode. PK data was analyzed using the WinNonlin program (ver. 5.2, Pharsight) compartmental models of analysis.

Figure 2:
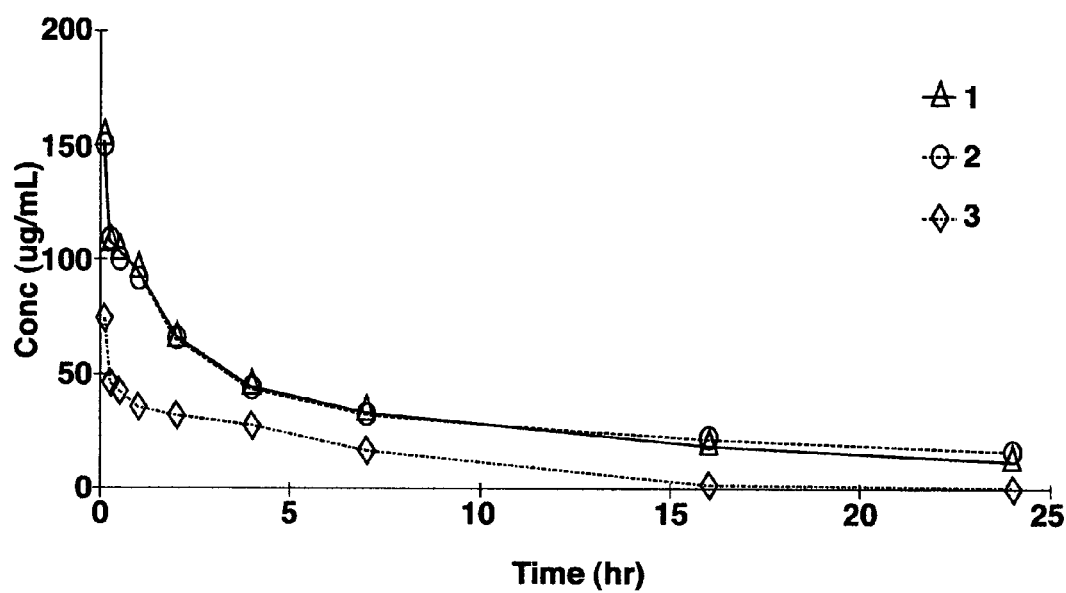
FIG. 2 shows mouse IV PK (pharmacokinetic) profiles of DAG-PEG formulations of PEG-12-acetyl-GDO (glycerol dioleate) and PEG-2-acetamido-GDO of rifampicin, and a rifampicin solution containing 5% dimethyl sulfoxide and 10% Cremophor EL.

FIG. 2 shows comparison between mouse PK profiles of various Rifampicine formulations administered intravenously. DAG-PEG formulations of (1) PEG-12-acetyl-GDO and (2) PEG-12-acetamido-GDO of rifampicin, as well as (3) a rifampicin solution containing 5% dimethyl sulfoxide and 10% Cremophor EL were tested. The drug was administered intravenously and the dosing strength was 20 mg/kg. The AUC (area under the curve) of the DAG-PEG formulations were (1) 878.6 μg·hr/mL and (2) 1061.5 μg·hr/mL versus 341.2 μg·hr/mL for the Cremophor EL solution (3).

Figure 3:
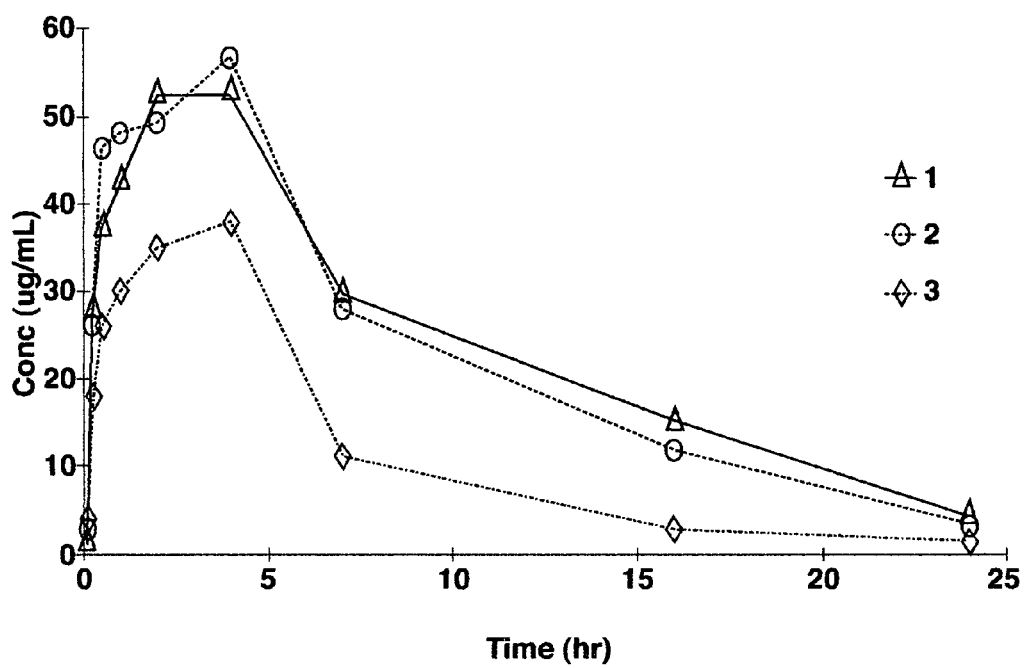
FIG. 3 shows mouse oral PK profiles of DAG-PEG formulations of PEG-12-acetyl-GDO and PEG-12-acetamido-GDO of rifampicin, a rifampicin solution containing 5% dimethyl sulfoxide and 10% Cremophor EL.

FIG. 3 shows a comparison between mouse PK profiles from oral administrations of the drug. The formulations and dose strength were the same as in FIG. 2. The relative bioavailability (based on $AUC_{0\ to\ 24\ hr}$ of PEG-12-acetyl-GDO) of the DAG-PEG formulations were (1) 71.6% and (2) 68.6% versus 29.8% for the Cremophor EL solution (3).

Figure 4:
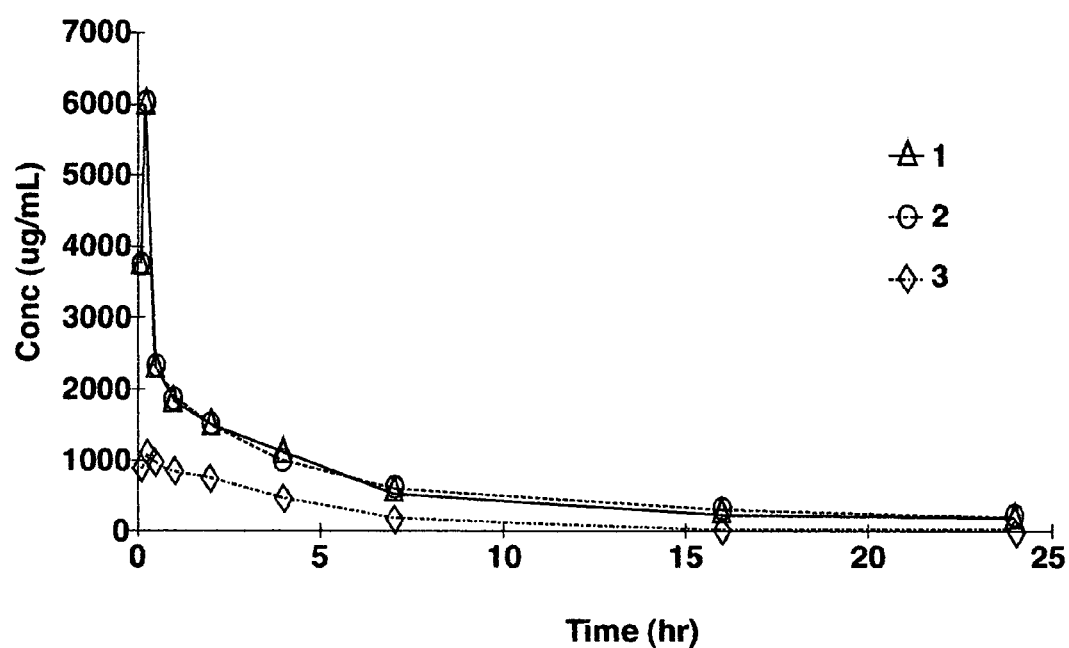
FIG. 4 shows rifampicin levels in lung in a mouse model after the drug was administered intravenously.

FIG. 4 shows a comparison among the drug level in lung after IV administration with (1) PEG-12-acetyl-GDO and (2) PEG-12-acetamido-GDO rifampicin liposomes and (3) a rifampicin solution containing 5% dimethyl sulfoxide and 10% Cremophor EL. The dosing strength was the same as in FIG. 2. After drawing blood for PK studies, mice were sacrificed at each time point and organs were removed. The drug was then extracted with organic solvent and tested with the same procedure as for PK plasma. Lung is one of the targets for TB treatment. Significant amounts of the drugs were delivered to the lung by the DAG-PEG formulations. The accumulated amounts (μg·hr/mg) of rifampicin for the DAG-PEG formulations were (1) 8095.8 and (2) 8624.7 versus 3902.1 for the Cremophor EL solution (3). The challenge is that the current sole commercial IV formulation requires administration of the drug within a few hours, otherwise the drug will be precipitated. Also, the drug is very toxic. The tested liposomal formulations are stable suspensions which can keep at room temperature for months without precipitation and also provide a better PK and lung delivery profile.

Figure 5:
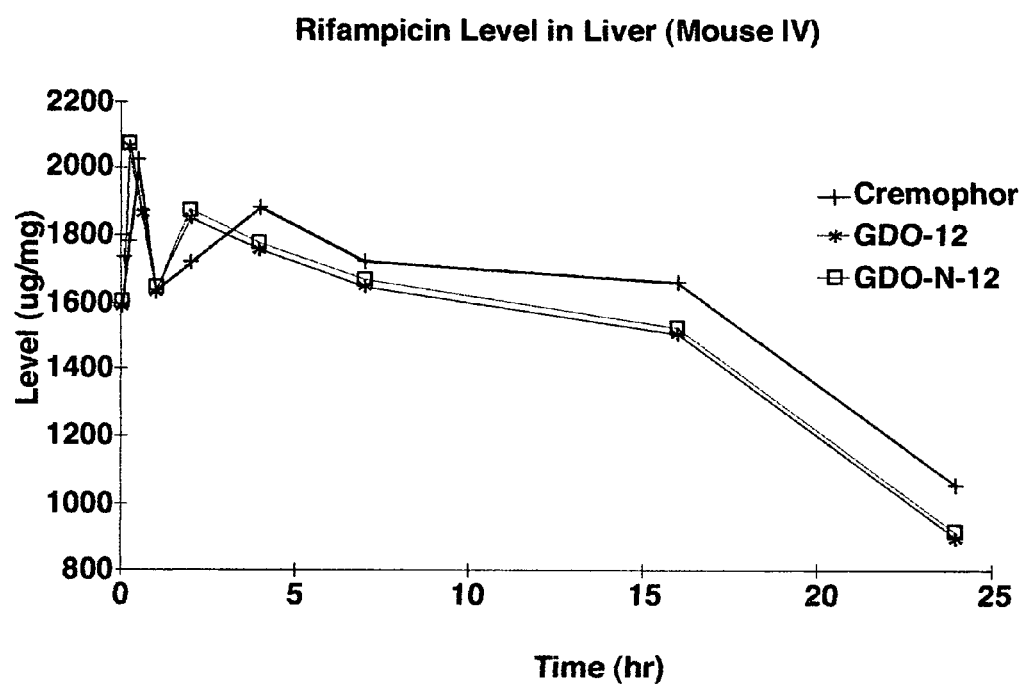
FIG. 5 shows rifampicin levels in liver in a mouse model after the drug was administered intravenously.

FIG. 5 shows a comparison among the drug level in liver after IV administration from (1) PEG-12-acetyl-GDO, (2) PEG-12-acetamido-GDO of rifampicin and (3) a rifampicin solution containing 5% dimethyl sulfoxide and 10% Cremophor EL. The dosing strength was the same as in FIGS. 2 and 4. The accumulated amounts (μg·hr/mg) of Rifampicin curve) of the DAG-PEG formulations were (1) 34595.7 and 36889.9 (2) versus 36177.2 for the Cremophor EL solution (3). The drug was not retained in the liver while large amounts of the drugs were delivered to the lung by the DAG-PEG formulations of (1) and (2).

The pharmacological activity of rifampin was considerably increased when it was encapsulated in the liposomes. Rifampin-liposomes delivered twice amounts into lung while having a similar profile in liver as compared to Cremophor solution. The new liposome formulations can appreciably increase the therapeutic efficacy of rifampin. These results clearly demonstrated that liposome targeting to macrophages can considerably increase the antitubercular activity of rifampin.

Example 28

Antifungal-Lipid Formulations

Tetrahydrofuran antibiotics are widely used as antifungal agents. They include the drug ketoconazole and are described in U.S. Pat. No. 5,039,676. Newer tetrahydrofurans have been developed that are more effective and less toxic than ketoconazole. They are described in U.S. Pat. No. 5,661,151. The newer tetrahydrofurans include posaconazole, voriconazole and itraconazole.

In addition to the agents described in U.S. Pat. No. 5,661,151, the class of tetrahydrofuran drugs includes a new tetrahydrofuran drug that is referred to herein as equaconazole. Equaconazole has the following structure(s).

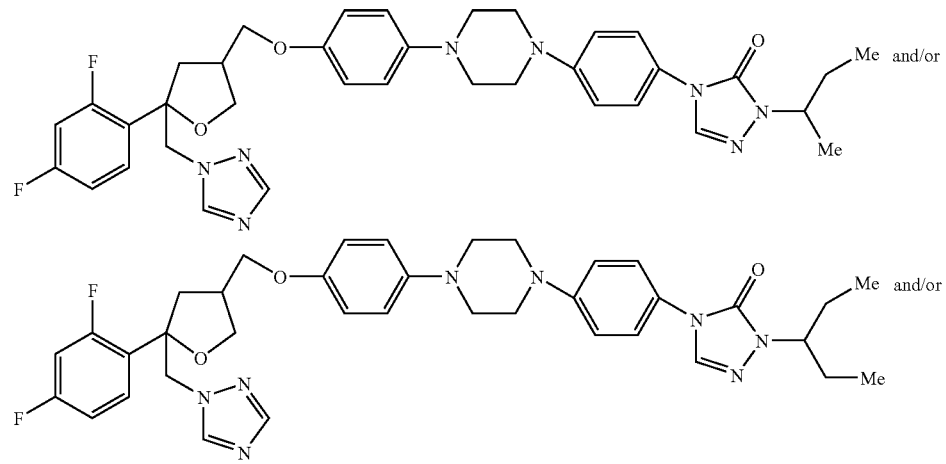

In this example, fungicide was combined in an aqueous solution with DAG-PEG lipids. A variety of drug-to-lipid ratios were tested, as well as a variety of formation temperatures. After mixing, formulations were allowed to stand at room temperature. The results are shown in Table 8.

TABLE 8

| (a) Lipid w/Posaconazole | Lipid Conc | Drug Solubility | | | |
|---|---|---|---|---|---|
| (30 mg drug/mL) | (mg/mL) | 25° C. | 35° C. | 45° C. | 60° C. |
| PEG-12-$N_3$-GDO | 120 | + | ++ | ++ | ++ |
| PEG-12-$N_3$-GDM | 120 | + | ++ | ++ | +++ |
| PEG-12-$N_3$-GDLO | 150 | + | ++ | ++ | +++ |
| PEG-12-$N_3$-GDP | 150 | + | ++ | ++ | +++ |

TABLE 8-continued

| | | | | | |
|---|---|---|---|---|---|
| PEG-12-Ac$_2$-GDO | 120 | + | ++ | ++ | +++ |
| PEG-12-Ac$_2$-GDM | 120 | + | ++ | ++ | +++ |

| | Drug Solubilized @ 40° C. | | | | |
|---|---|---|---|---|---|
| (b) Lipid w/Posaconazole (30 mg drug/mL) | L/D Ratio = 1 | L/D Ratio = 3 | L/D ratio = 5 | L/D ratio = 10 | L/D ratio = 20 |
| PEG-12-N$_3$-GDO | –/+ | + | ++ | +++ | ++ |
| PEG-12-N$_3$-GDM | –/+ | + | ++ | +++ | ++ |
| PEG-12-N$_3$-GDLO | –/+ | + | ++ | +++ | +++ |
| PEG-12-N$_3$-GDP | –/+ | + | ++ | +++ | +++ |
| PEG-12-Ac$_2$-GDO | –/+ | + | ++ | ++ | ++ |
| PEG-12-Ac$_2$-GDM | –/+ | + | ++ | ++ | ++ |

Example 29

Equaconazole-Lipid Formulations

Equaconazole was combined in an aqueous solution with DAG-PEG lipids. A variety of drug-to-lipid ratios were tested, as well as a variety of formation temperatures. After mixing, formulations were allowed to stand at room temperature. The results are shown in Table 9.

TABLE 9

| (a) Lipid w/Equaconazole | Lipid Conc | Drug Solubility[1] | | | |
|---|---|---|---|---|---|
| (30 mg drug/mL) | (mg/mL) | 25° C. | 35° C. | 45° C. | 60° C. |
| PEG-12-N$_3$-GDO | 120 | + | ++ | ++ | ++ |
| PEG-12-N$_3$-GDM | 120 | + | ++ | ++ | +++ |
| PEG-12-N$_3$-GDLO | 120 | + | ++ | ++ | +++ |
| PEG-12-N$_3$-GDP | 150 | + | ++ | ++ | +++ |
| PEG-12-Ac$_2$-GDO | 120 | + | ++ | ++ | +++ |
| PEG-12-Ac$_2$-GDM | 120 | + | ++ | ++ | +++ |

| | Drug Solubilized @ 40° C. | | | | |
|---|---|---|---|---|---|
| (b) Lipid w/Equaconazole (30 mg drug/mL) | L/D ratio = 1 | L/D ratio = 3 | L/D ratio = 5 | L/D ratio = 10 | L/D ratio = 20 |
| PEG-12-N$_3$-GDO | –/+ | + | ++ | +++ | ++ |
| PEG-12-N$_3$-GDM | –/+ | + | ++ | +++ | ++ |
| PEG-12-N$_3$-GDLO | –/+ | + | ++ | +++ | +++ |
| PEG-12-N$_3$-GDP | –/+ | + | ++ | +++ | +++ |
| PEG-12-Ac$_2$-GDO | –/+ | + | ++ | ++ | ++ |
| PEG-12-Ac$_2$-GDM | –/+ | + | ++ | ++ | ++ |

In Tables 8 and 9, "–" means not soluble; "–/+" means partially soluble; "+" soluble, "++" very soluble, "+++" most soluble. L/D ratio means lipid to drug ratio.

Example 30

Antifungal Oral Solution

PEG lipid was added to a vessel equipped with a mixer propeller. The drug substance was added with constant mixing. Mixing continued until the drug was visually dispersed in the lipids. Pre-dissolved excipients were slowly added to the vessel with adequate mixing. Mixing continued until fully a homogenous solution was achieved. A sample formulation is described in Table 10.

TABLE 10

| Ingredient | mg/mL |
|---|---|
| Antifungal Active | 30.0 |
| PEG Lipid | 100 |
| Lactic Acid | 50 |
| Sodium Hydroxide | See below |
| Hydrochloric Acid | See below |

TABLE 10-continued

| Ingredient | mg/mL |
|---|---|
| Sodium Benzoate | 2.0 |
| Artificial Flavor | 5.0 |
| Purified Water | qs 1 mL |

The drug may be itraconazole, posaconazole, voriconazole or equaconazole. The lipid may be PEG-12-N$_3$-GDO, PEG-12-N$_3$-GDM, PEG-12-N$_3$-GDLO, PEG-12-N$_3$-GDP, PEG-12-Ac$_2$-GDO, PEG-12-Ac$_2$-GDM or any combination thereof Sodium hydroxide is used to prepare a 10% w/w solution in purified water. The targeted pH is in a range of 4.0 to 7.0. NaOH is used to adjust pH if necessary.

Example 31

Antifungal IV Injectable Solution

The IV solution was prepared as in Example 26, except that the targeted pH range was between 6.5 and 7.5. A sample formulation is described in Table 11.

TABLE 11

| Ingredient | mg/mL |
|---|---|
| Antifungal Active | 30.0 |
| PEG Lipid | 100 |
| Sodium Hydroxide | See Below |
| Lactic Acid | 50 |
| Purified Water | qs 1 mL |

The drug may be itraconazole, voriconazole, posaconazole or equaconazole. The lipid may be PEG-12-$N_3$-GDO, PEG-12-$N_3$-GDM, PEG-12-$N_3$-GDLO, PEG-12-$N_3$-GDP, PEG-12-$Ac_2$-GDO, PEG-12-$Ac_2$-GDM or any combination thereof. Sodium hydroxide is used to prepare a 10% w/w solution in purified water. The targeted pH is in a range of 6.5 to 7.0. NaOH is used to adjust pH if necessary.

Example 32

Pharmacokinetic Profile and Bioavailability of Posaconazole Formulations

Groups of three male mice (B6D2F1) were used for the studies. Pharmacokinetics (PK) were performed on heparinized mouse plasma samples obtained typically at 0 hr, 0.08 hr, 0.25 hr, 0.5 hr, 1 hr, 2 hr, 4 hr, 8 hr, 16 hr and 24 hr after the bolus IV injection or oral feeding for posaconazole and at 0 hr, 0.08 hr, 0.25 hr, 0.5 hr, 1 hr, 2 hr, 4 hr, 8 hr, 16 hr and 24 hr for itraconazole. Samples were analyzed using a HPLC-MS method. To determine the level of each drug, the drug was first isolated from plasma with a sample pre-treatment. Acetonitrile were used to remove proteins in samples. An isocratic HPLC-MS method was then used to separate the drugs from any potential interference. Drug levels were measured by MS detection with a multiple reaction monitoring (MRM) mode. PK data was analyzed using the WinNonlin program (ver. 5.2, Pharsight) compartmental models of analysis.

Figure 6:
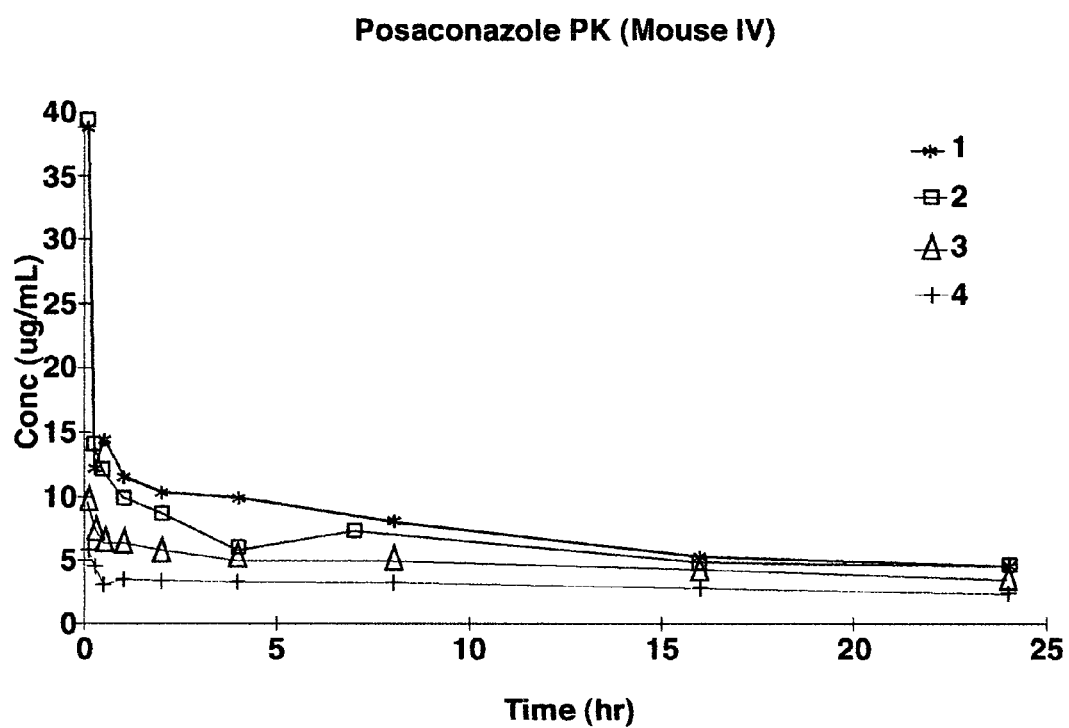
FIG. 6 shows mouse IV PK profiles of posaconazole with formulation of PEG-12-acetamido ($N_3$)-GDO (1:3 drug to lipid ratio) and PEG-12-acetamido ($N_3$)-GDM (1:5 drug to lipid ratio), POPC (1-Palmitoyl,2-oleoyl-sn-Glycero-3-phosphocholine, 1:1 drug to lipid ratio) and a posaconale solution containing 5% dimethyl sulfoxide and 10% Cremophor EL.

FIG. 6 shows mouse PK profiles of posaconazole formulations with (1) PEG-12-acetamido ($N_3$)-GDO (1:3 drug to lipid ratio) and (2) PEG-12-acetamido ($N_3$)-GDM (1:5 drug to lipid ratio), (3) palmitoyl-oleayl phosphatidylcholine, or POPC, (1:1 drug to lipid ratio) and (4) a posaconale solution containing 5% dimethyl sulfoxide and 10% Cremophor. The drug was administered intravenously and the dosing strength was 10 mg/kg. The AUC were 289.3 µg·hr/mL and 287.5 µg·hr/mL for the DAG-PEG formulations (1) and (2), respectively, and 164.1 µg·hr/mL and 193.2 µg·hr/mL for formulations of (3) and (4), respectively.

Figure 7:
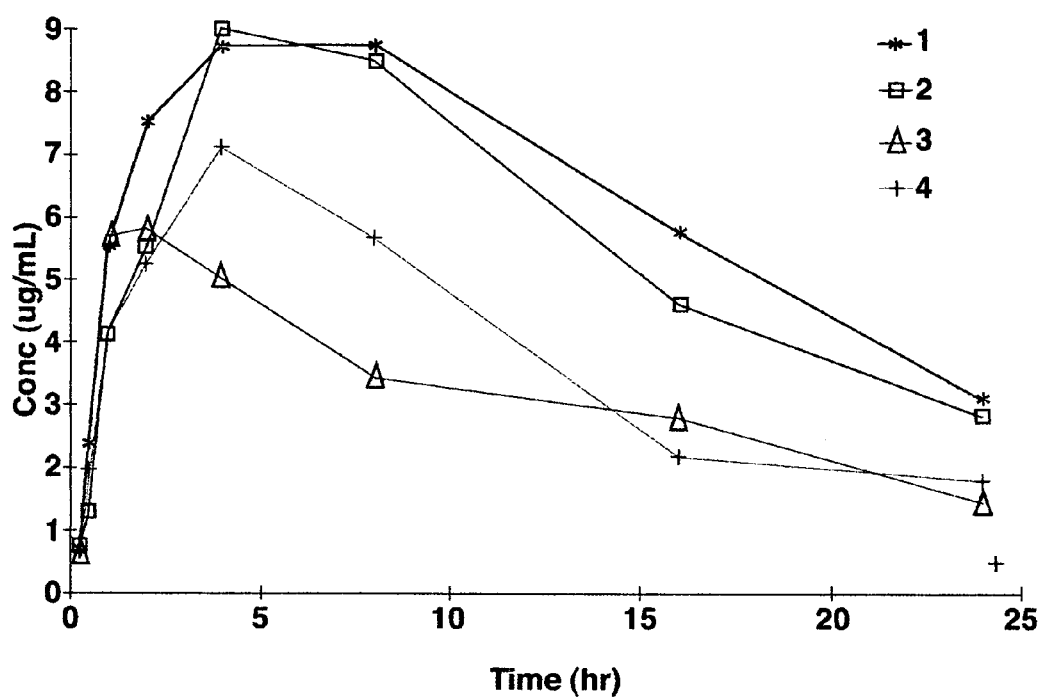
FIG. 7 shows mouse oral PK profiles of posaconazole with formulation of PEG-12-acetamido ($N_3$)-GDO (1:3, drug to lipid ratio) and PEG-12-acetamido-GDM (1:5, drug to lipid ratio), the commercial product (Noxifil®, Schering-Plough), and a posaconazole solution containing 5% dimethyl sulfoxide and 10% Cremophor EL.

FIG. 7 shows mouse PK profiles of posaconazole formulations with (1) PEG-12-acetamido ($N_3$)-GDO (1:3, drug to lipid ratio) and (2) PEG-12-acetamido ($N_3$)-GDM (1:5, drug to lipid ratio), (3) a commercial product and (4) a posaconazole solution containing 5% dimethyl sulfoxide and 10% Cremophor. The drug was administered orally and the dosing strength was 50 mg/kg. The relative bioavailability (based on the $AUC_{0-24\,hr}$ of the Cremophor formulation) were 53.8.% and 49.7% for the formulations of PEG-DAG (1) and (2), 33.2% and 38.8% for the formulations of (3) and (4), respectively.

Example 33

Antifungal Topical Cream

PEG lipid was added to a stainless steel vessel equipped with propeller type mixing blades. The drug substance was added with constant mixing. Mixing continued until the drug was visually dispersed in the lipids at a temperature to 60°-65° C. Organic acid, Cholesterol and glycerin were added with mixing. Ethanol and ethyoxydiglycol were added with mixing. Finally Carbopol ETD 2020, purified water and triethylamine were added with mixing. Mixing continued until fully a homogenous cream was achieved. The formulation is described in Table 12.

TABLE 12

| Ingredient | % |
|---|---|
| Antifungal Active | 1.0 |
| PEG Lipid | 5.0 |
| Carbopol ETD 2020 | 0.5 |
| Ethyoxydiglycol | 1.0 |
| Ethanol | 5.0 |
| Glycerin | 1.0 |
| Cholesterol | 0.4 |
| Triethylamine | 0.20 |
| Organic acid | 10 |
| Sodium hydroxide | See below |
| Purified water | qs 100 |

The drug may be itraconazole, posaconazole, voriconazole or equaconazole. The lipid may be PEG-12-$N_3$-GDO, PEG-12-$N_3$-GDM, PEG-12-$N_3$-GDLO, PEG-12-$N_3$-GDP, PEG-12-$Ac_2$-GDO, PEG-12-$Ac_2$-GDM or any combination thereof. Organic acid may be lactic acid or pyruvic acid or glycolic acid. Sodium hydroxide is used to adjust pH if necessary. The targeted pH range was between 3.5 and 7.0.

Example 34

Antifungal Topical Solution

The topical solution was prepared as in Example 33, except that active was first dissolved in organic acid and ethanol. A sample formulation is described in Table 13.

TABLE 13

| Ingredient | % |
|---|---|
| Antifungal Active | 1.0 |
| PEG Lipid | 5.0 |
| α-Tocopherol | 0.5 |
| Organic acid | 10.0 |
| Ethanol | 5.0 |
| Sodium Benzoate | 0.2 |
| Sodium Hydroxide | See Below |
| Purified Water | qs 100 |

The drug may be itraconazole, posaconazole, voriconazole or equaconazole. The lipid may be PEG-12-$N_3$-GDO, PEG-12-$N_3$-GDM, PEG-12-$N_3$-GDLO, PEG-12-$N_3$-GDP, PEG-12-$Ac_2$-GDO, PEG-12-$Ac_2$-GDM or any combination thereof. Organic acid may be lactic acid or pyruvic acid or glycolic acid. Sodium hydroxide is used to adjust pH if necessary. The targeted pH range was between 3.5 and 7.0.

In another aspect, the invention comprises a method of solubilizing a water-insoluble agent, i.e., a drug compound that, because of low solubility in water, typically requires formulation with a pharmaceutically acceptable carrier for effective delivery to an intended site of action. Such delivery may be intravenous, oral, topical, subdermal, sublingual, or any other mode of drug delivery. The invention also includes compositions for such delivery. Both the methods and the compositions related to delivery of water-insoluble agents employ the PEG-lipid conjugates of the present invention and the methods and materials described above.

While preferred embodiments of the present invention have been described, those skilled in the art will recognize that other and further changes and modifications can be made without departing from the spirit of the invention, and all such changes and modifications should be understood to fall within the scope of the invention.

We claim:

1. A compound represented by the formula

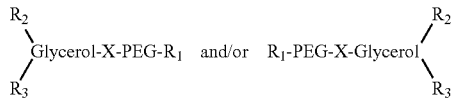

where R1 is either —OH or —OCH3;

where R2 and R3 are alkyl groups having between 6 and 22 carbons; and where X is amino.

2. The compound of claim 1 where R2 and R3 are selected from the group consisting of oleate, myristate, linoleate and palmitate.

3. The compound of claim 1 where the PEG chain consists of between about 6 and 45 subunits.

4. The compound of claim 3 where the PEG chain consists of between about 8 and 23 subunits.

5. The compound of claim 3 where the PEG chain consists of between about 12 and 23 subunits.

* * * * *